United States Patent [19]

Peterson

[11] 4,408,493

[45] Oct. 11, 1983

[54] DIRECTIONAL ULTRASONIC TRANSDUCERS

[75] Inventor: William E. Peterson, Thousand Oaks, Calif.

[73] Assignee: Rockwell International Corporation, El Segundo, Calif.

[21] Appl. No.: 361,319

[22] Filed: Mar. 24, 1982

[51] Int. Cl.$^3$ ............................................. G01N 29/04
[52] U.S. Cl. .................................................. 73/643
[58] Field of Search ........................... 73/643; 333/119

[56] References Cited

U.S. PATENT DOCUMENTS

| | | | |
|---|---|---|---|
| 3,850,028 | 11/1974 | Thompson et al. | 73/643 |
| 4,048,847 | 9/1977 | Alers et al. | 73/643 |
| 4,080,836 | 3/1978 | Thompson et al. | 73/643 |
| 4,104,922 | 8/1978 | Alers et al. | 73/643 |
| 4,127,035 | 11/1978 | Vasile | 73/643 |
| 4,218,924 | 8/1980 | Fortunko et al. | 73/643 |
| 4,232,557 | 11/1980 | Vasile | 73/643 |
| 4,295,214 | 10/1981 | Thompson | 73/643 |
| 4,307,615 | 12/1981 | Robinson | 73/643 |

OTHER PUBLICATIONS

Fredrick, Useful Relationships in 180° Hybrids, Anzac Electronics Technical Note, p. 225.
Freeman, Hybrid Transformers—Part 1, Telecommunications Journal of Australia, vol. 27, p. 246 (1977).

*Primary Examiner*—Howard A. Birmiel
*Attorney, Agent, or Firm*—H. Fredrick Hamann; Craig O. Malin; John J. Deinken

[57] ABSTRACT

An apparatus for generating acoustic waves of wavelength $\lambda$ in an electrically conductive object includes an electromagnetic acoustic transducer, with a source of magnetic flux for producing a magnetic field in the object, a first periodic coil within the field, and a second periodic coil within the field and offset from the first coil by $\lambda/4$. A first port of a four port hybrid is connected to the first coil and a second port is connected to the second coil, with a 90° phase delay element interposed between the first port and the first coil. A signal generator provides an input signal at a frequency corresponding to $\lambda$, with a transmitter for applying the signal to either a third or a fourth port of the hybrid to generate a unidirectional wave in one of two opposite directions. An apparatus for detecting acoustic waves includes a first receiver connected to the third port and a second receiver connected to the fourth port.

16 Claims, 7 Drawing Figures

DIRECTIONAL ULTRASONIC TRANSDUCERS

BACKGROUND OF THE INVENTION

This invention relates to techniques for generating and detecting ultrasonic waves.

Efficiency and economy have been increasingly emphasized in many aspects of modern structural design, and this emphasis has stimulated the more widespread use of nondestructive testing techniques. Before nondestructive methods were developed, it was necessary to assume, in designing structural components, that flaws of a certain size were present in the construction materials. This design technique required the selection of structural components which were of sufficient size and adequate in strength to withstand failure even if the assumed defects were present. The introduction of nondestructive testing methods, however, has made feasible the identification of a structural defect at an early stage in the life of the underlying flaw, so that the appropriate corrective action, such as removing and replacing a defective component, can be accomplished before the defect causes a catastrophic failure. Consequently, where nondestructive testing can be implemented throughout their operational lives, structural components may be manufactured and assembled more economically by reducing dimensions and substituting lower strength, less expensive materials. Nondestructive inspection techniques can thus be utilized to maintain a desired level of reliability in a structure while concurrently reducing construction and materials costs. Nondestructive testing can similarly be used to extend the service life of existing structures.

One of the most useful types of nondestructive testing involves ultrasonics, in which the interactions between acoustic wave energy and the internal structure of an object are analyzed to predict the physical integrity of the object. A key element in an ultransonic nondestructive testing system is the transducers, which are used to convert electrical energy into acoustic wave energy in the test object and also to convert the acoustic energy back into electrical energy for detection purposes. Traditionally, the high conversion efficiency and modest cost of piezoelectric materials have influenced their widespread use as ultrasonic transducers in many applications. Piezoelectric transducers are disadvantaged, however, by their need to be coupled to the ultrasonic medium through a liquid or solid bond.

Because of these limitations to the piezoelectric approach, applications with demanding performance requirements, such as, for example, operation at high speeds, at elevated temperatures, in remote locations, with broadband and reproducible acoustic coupling, and without the subsequent cleanup of a liquid bond, have spurred the development of noncontact ultrasonic methods, such as electrostatic tranducers, optical techniques, and electromagnetic transducers. These techniques have supplanted piezoelectric transducers in many applications. One of the most promising noncontact transducers is the electromagnetic acoustic transducer (EMAT). An EMAT consists of an electrically conductive coil which is positioned within a static magnetic field extending into the surface of a conducting material. When a radio frequency signal is applied to the coil, eddy currents are induced in the material. If the magnetic field and the coil are properly oriented, the Lorentz forces which are exerted on the eddy currents by the magnetic field will be transferred to the lattice structure of the material and thereby generate an ultrasonic wave. Reduced inspection time, an ability to operate in remote and inaccessible locations, and diminished transducer wear are some of the significant advantages offered by an EMAT-based nondestructive testing system.

EMATs have been fabricated with a variety of coil and magnet configurations to suit the requirements of particular applications. U.S. Pat. Nos. 3,850,028; 4,048,847; 4,080,836; 4,092,868; 4,104,922; 4,127,035; 4,184,374; 4,218,924; 4,232,557; 4,248,092; 4,295,214; and 4,296,486, for example, the teachings of which are incorporated herein by reference, illustrate some of the approaches which have been utilized.

EMATs have been employed to great advantage in a number of nondestructive testing situations, and ongoing research is continuing to identify additional applications for these devices. One of the goals of this research is to improve the signal to noise ratio of EMAT systems by increasing the amplitude of the acoustic energy which can be generated by an EMAT and by increasing the signal level produced by an EMAT in detecting acoustic energy at a given amplitude. In particular, a need has developed for a practical system which would enable an EMAT to generate a highly directional beam of acoustic energy or selectively detect only that acoustic energy propagating in a particular direction.

SUMMARY OF THE INVENTION

It is a general objective of this invention to provide an improved technique for ultrasonic nondestructive evaluation.

The invention provides an apparatus for interacting with acoustic wave energy of wavelength $\lambda$ in an electrically conductive object. This apparatus includes an electromagnetic acoustic transducer, with a source of magnetic flux for producing a magnetic field extending into the object. The transducer also includes first and second periodic coils located within the field, with the coils offset from each other. The first port of a four port hybrid is connected to the first coil and a second port of the hybrid is connected to the second coil, with a phase delay element interposed between the first port and the first coil.

In a more particular embodiment for generating acoustic waves, the coils are offset by $\lambda/4$ and the phase delay is a 90° phase delay. A signal generator provides an input signal at a frequency corresponding to the wavelength $\lambda$ and a transmitter receives, amplifies, and applies the signal to the hybrid, thereby generating the waves in a first direction in the object when the signal is applied to a third port of the hybrid and in a direction opposite to the first direction when the signal is applied to a fourth port of the hybrid.

The generating embodiment may further include a second four port hybrid interposed between the first hybrid and the coils so that the first coil is connected through the phase delay element to a first port of the second hybrid, the second coil is connected to a second port of the second hybrid, the first port of the first hybrid is connected to a summing third port of the second hybrid, and the second port of the first hybrid is connected to a differencing fourth port of the second hybrid.

In a more particular embodiment for detecting acoustic waves, the coils are again offset by $\lambda/4$ and the phase delay provides a delay of 90°. A first receiver is connected to a third port of the hybrid to detect acoustic wave energy at the wavelength λ which is propagating in a first direction in the object, and a second receiver is connected to a fourth port of the hybrid to detect waves propagating in a direction opposite to the first direction.

The invention also provides a method of generating acoustic energy at a wavelength λ in an electrically conductive object, which involves the steps of establishing a magnetic field extending into the object, positioning a first periodic coil within the field, positioning a second periodic coil with the field and offset from the first coil, connecting first and second ports of a four port hybrid to the first and second coils, respectively, introducing a phase delay between the hybrid and the first coil, generating an input signal at a frequency corresponding to the wavelength λ, and transmitting the input signal to a third port of the hybrid.

A method of detecting acoustic energy is similar, except that the steps of generating and transmitting are replaced by the step of connecting a first receiver to a third port of the hybrid.

BRIEF DESCRIPTION OF THE DRAWINGS

Additional objectives, features, and advantages of the invention are discussed in the detailed description below, which is supplemented by the drawings, wherein.

DETAILED DESCRIPTION OF THE INVENTION

Figure 1:
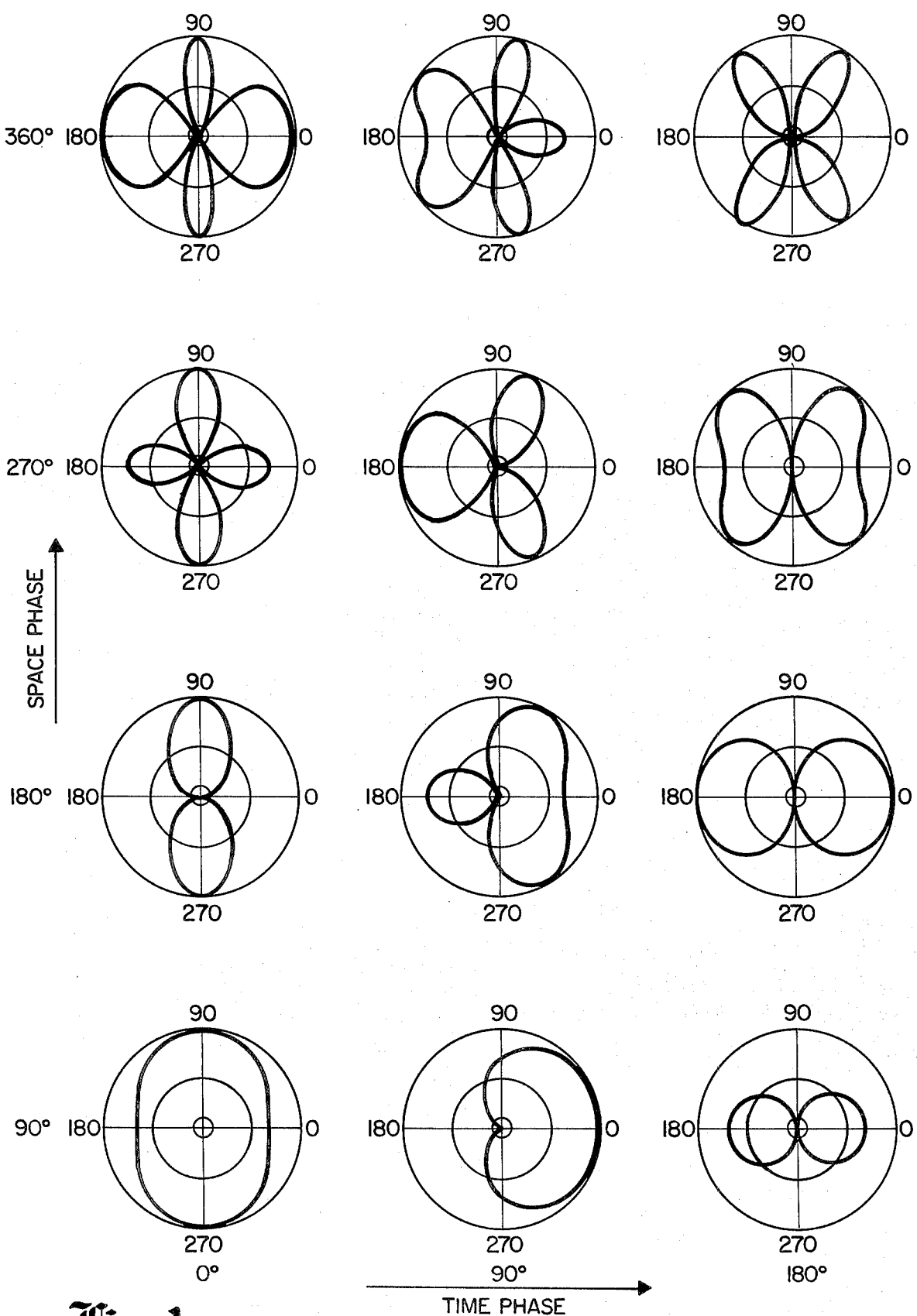
FIG. 1 illustrates some of the possible beam patterns for two spaced and phased RF antennas.

It is well known in the radio frequency antenna art that if two antennas are spaced apart a distance of one fourth wavelength (90°) for a particular frequency and one is driven with a signal at that frequency which is 90° out of phase with respect to a signal at that frequency applied to the second antenna, a unidirectional beam will be transmitted. Other combinations of space phase (the distance between the antennas) and time phase may be used to produce different beam patterns. A 90° spatial phase between the antennas together with signals which are 180° out of phase, for example, will produce a bidirectional beam. Some examples of the possible beam patterns are illustrated in FIG. 1 for various combinations of spacing and phase delay. The applicability of this principle to produce unidirectional ultrasonic waves with electromagnetic acoustic transducers (EMATs) is known, as disclosed in U.S. Pat. No. 4,295,214. It is an outstanding feature of the present invention to expand upon this application by utilizing hybrid circuit elements to provide an improved method and apparatus for generating and detecting acoustic wave energy.

A hybrid is a passive, lossless, reciprocal circuit element. The particular embodiments of the invention illustrated herein utilize a 180° four port hybrid, such as the hybrid illustrated in schematic form in FIG. 2, although those skilled in the art will appreciate that other types of hybrids might be used as well in the invention. The 180° hybrid is commonly known by a variety of different names, i.e, magic tee, 3 db coupler, hybrid junction, hybrid coil, iso-T, null-T, power divider, or power combiner. In order to operate properly, the impedance of all four ports of the hybrid, which are identified as A, B, C, and D in FIG. 1, must be matched. To use the hybrid as a two way, in phase (0°) power divider/summer (iso-T), port B is terminated to ground through the proper impedance. Then a signal applied at port A will divide evenly between ports C and D. Conversely, signals applied simultaneously at ports C and D will add and their sum will be output at port A. If port A is terminated, the hybrid becomes a two way, out of phase (180°) power divider/summer (null-T) and a signal applied to port B will divide between ports C and D, with the output at C being in phase with the input, while the output at D will be 180° out of phase with the input. In any configuration, ports A and B will always be isolated from one another, as will ports C and D. These properties of the hybrid are summarized in Table 1 for the power divider arrangement and in Table 2 for the power summer.

TABLE I

POWER DIVIDER RELATIONSHIPS

| Input Signal | Input Port | Output Signals Port A | Port B | Port C | Port D |
|---|---|---|---|---|---|
| E cos ωt | A | — | 0 | $\frac{1}{\sqrt{2}}$ E cos ωt | $\frac{1}{\sqrt{2}}$ E cos ωt |
|  | B | 0 | — | $\frac{1}{\sqrt{2}}$ E cos ωt | $\frac{1}{\sqrt{2}}$ E cos (ωt + 180°) |
|  | C | $\frac{1}{\sqrt{2}}$ E cos ωt | $\frac{1}{\sqrt{2}}$ E cos ωt | — | 0 |
|  | D | $\frac{1}{\sqrt{2}}$ E cos ωt | $\frac{1}{\sqrt{2}}$ E cos (ωt + 180°) | 0 | — |

TABLE II

POWER SUMMER RELATIONSHIPS

| Input Signal | Input Port | Port A | Port B | Port C | Port D |
|---|---|---|---|---|---|
| $E \cos \omega t$ | A | — | — | $\sqrt{2} E \cos \omega t$ | 0 |
| $E \cos \omega t$ | B | | | | |
| $E \cos \omega t$ | A | — | — | 0 | $\sqrt{2} E \cos \omega t$ |
| $E \cos (\omega t + 180°)$ | B | | | | |
| $E \cos \omega t$ | C | $\sqrt{2} E \cos \omega t$ | 0 | — | — |
| $E \cos \omega t$ | D | | | | |
| $E \cos \omega t$ | C | 0 | $\sqrt{2} E \cos \omega t$ | — | — |
| $E \cos (\omega t + 180°)$ | D | | | | |
| $E \cos \omega_2 t$ | A | — | — | $\frac{1}{\sqrt{2}} E (\cos \omega_1 t + \cos \omega_2 t)$ | $\frac{1}{\sqrt{2}} E (\cos \omega_1 t + \cos \omega_2 t)$ |
| $E \cos \omega_1 t$ | B | | | | |

Figure 3:
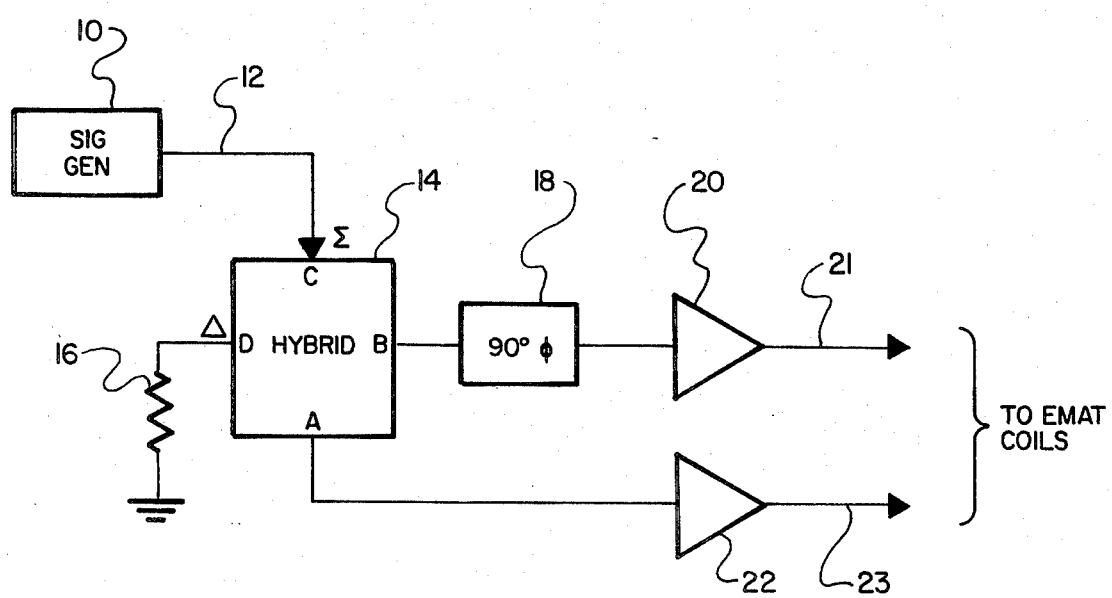
FIG. 3 is a schematic of an embodiment of the invention for generating unidirectional acoustic waves.

FIG. 3 is a schematic illustrating one embodiment of the present invention which may be used to generate acoustic waves in an electrically conductive object. A signal generator 10 provides an output signal on the line 12 at a frequency selected to correspond to the desired wavelength λ which is to be generated in the object. This signal is applied to the summing port C of a 180° four port hybrid 14. The differencing port D of the hybrid is terminated to ground through a matching impedance 16. The hybrid then divides the signal 12 between the output ports A and B. The portion on port B is delayed in phase by 90° by a phase delay element 18, and the two signals are then amplified by transmitters 20 and 22. The boosted signals are then applied, via lines 21 and 23, to the offset coils of an electromagnetic acoustic transducer (EMAT), such as the EMAT illustrated in FIG. 4.

Figure 2:
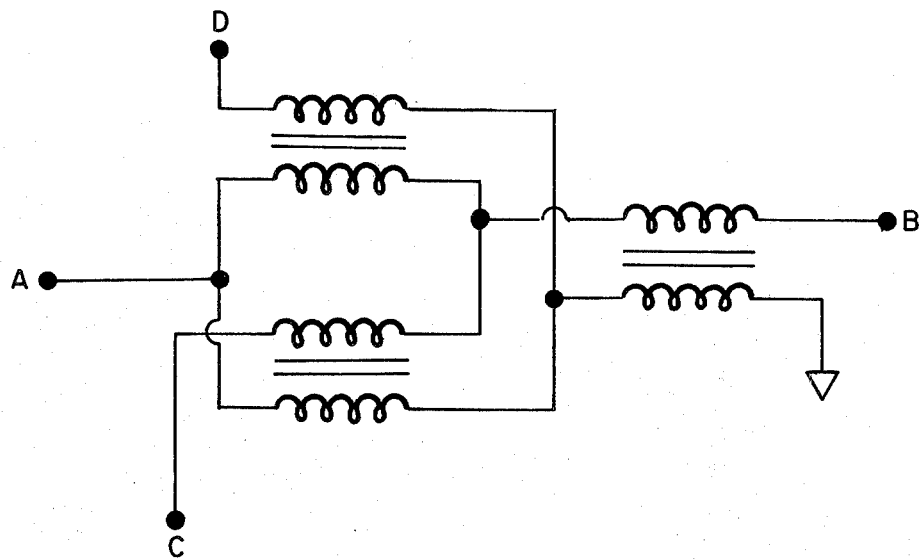
FIG. 2 is a schematic drawing of a typical four port hybrid circuit which may be used in the invention.
Figure 4:
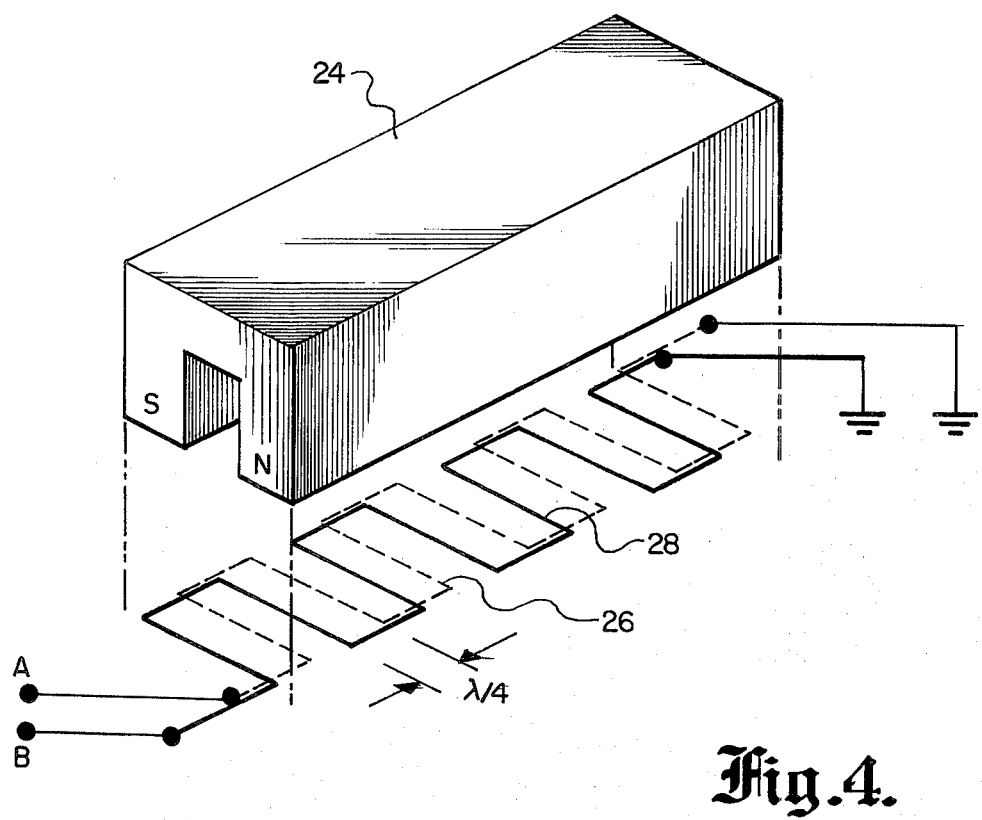
FIG. 4 is a perspective drawing of 90° offset dual EMAT coils.

FIG. 4 is a partially schematic perspective view of an EMAT which may be used with the embodiment shown in FIG. 2 to generate horizontally polarized shear (SH) waves. As will be appreciated by those skilled in the art, other EMAT configurations may be used to produce different types of ultrasonic waves. A magnet 24 provides a source of magnetic flux. A first periodic coil 26 and a second periodic coil 28 are positioned within the field of the magnet 24 with an offset between the coils of λ/4. The first coil 26 is connected to the output from port A of the hybrid 14 and the second coil 28 is connected to the 90° delayed output from port B. Since the second coil spatially lags the first coil by λ/4 (90°), this combination will result in destructive interference between the multiple waves generated in the object in one direction by the various segments of the coils. Conversely, the coil portions will generate waves in the opposite direction which will add, resulting in the generation of a unidirectional wave, analogous to the unidirectional radio wave antenna system discussed above.

Should it be desirable to reverse the direction of the generated beam of acoustic energy, this can be accomplished by connecting the signal generator 10 to the differencing port D and terminating the summing port C, or by reversing the connections to the coils, so that the first coil 26 is connected to port B and the second coil 28 is connected to port A. Consequently, the device of FIGS. 3 and 4 can be used to generate a highly directional beam of acoustic wave energy in a conductive object.

The embodiment of FIG. 3 was tested with a signal generator which provided pulsed signals at a frequency of 250 kHz. These signals were amplified to a level of 16 amps peak to peak and applied to an EMAT similar to that shown in FIG. 4, with each coil having four periods. This system was used to generate SH waves in a 1 inch thick sample of aluminum approximately 24 inches long and 6 inches wide. A conventional, single coil EMAT receiver was placed on the sample and two sets of measurements were taken. First, the transmitter was used to generate a unidirectional beam away from the receiver EMAT, so that the beam was reflected from an end of the sample and then detected by the receiver. The direction of the generated beam was then reversed so that the beam propagated directly to the receiver. A comparison between these two measurements indicated that a signal to noise ratio of approximately 18.3 dB was obtained.

Figure 5:
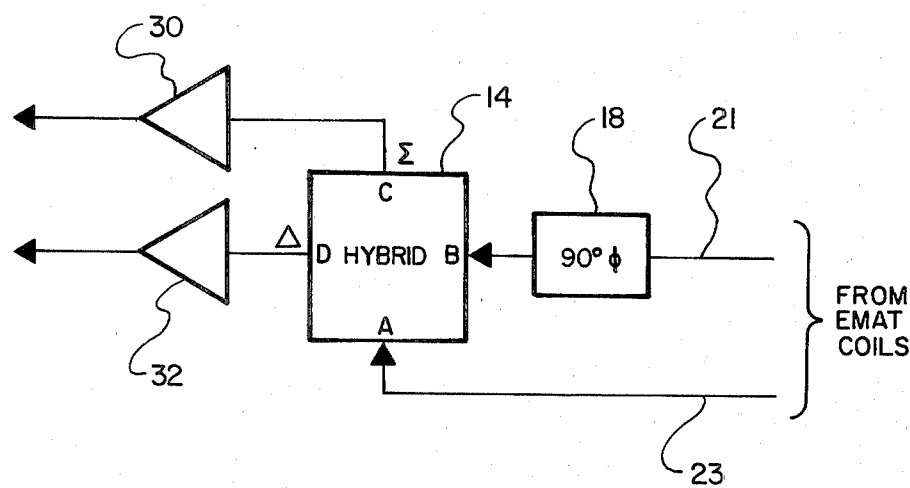
FIG. 5 is a schematic of an embodiment of the invention for bidirectionally detecting acoustic waves.

Another embodiment of the invention is shown in schematic form in FIG. 5. An EMAT such as that shown in FIG. 4 is again employed, but in this configuration the EMAT detects acoustic wave energy by producing corresponding electrical signals on the coils 26 and 28. These signals are connected, by lines 21 and 23, to ports A and B of the hybrid 14, with the signal to port B being delayed in phase 90° by the phase delay element 18. The summed output from port C is applied to a first receiver 30, while the differenced output from port D is applied to a second receiver 32. Thus, in this configuration, the invention permits the simultaneous detection of ultrasonic wave travelling in opposite directions, with the ability to distinguish those waves from each other. This capability has particular utility in nondestructive testing applications where signals propagating in opposite directions convey different information. A signal from one direction, for example, might represent a reflection from a flaw, while a signal from the other direction could indicate a reflection from an edge of the object being inspected.

Figure 6:
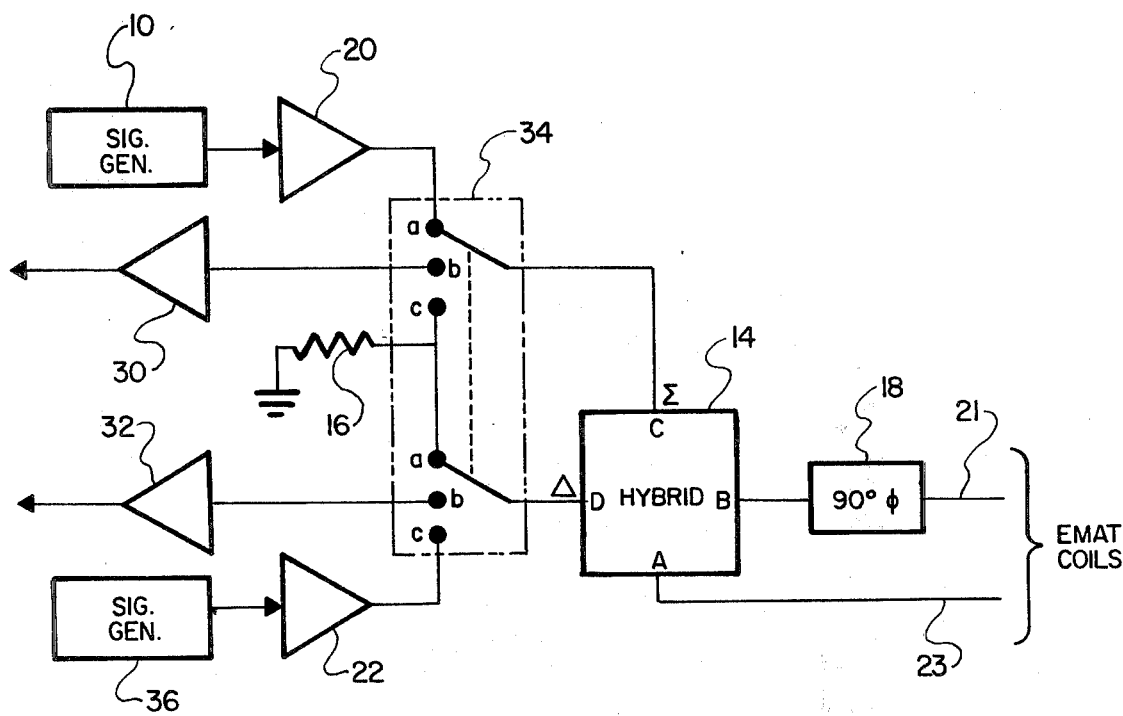
FIG. 6 is a schematic of an embodiment of the invention for selectively generating unidirectional acoustic waves or detecting bidirectional acoustic waves.

The embodiment of FIG. 6 provides the capability of both generating and detecting acoustic wave energy. Ports A and B are connected to the offset coils of a dual coil EMAT, as shown in FIG. 4, with the connection to port B being delayed 90° by the phase delay element 18. The summing port C and the differencing port D may be switched among several alternative connections. With a switch 34 in position a as shown, port C receives the output of the signal generator 10 as amplified by the transmitter 20. In this configuration the apparatus will operate to generate acoustic wave energy in a first direction. With the switch 34 in the lowest, or c position, the signal from a signal generator 36 will be amplified by the transmitter 22 and applied to port D to generate acoustic waves in a direction opposite to the first direction. Note that in either of these switch positions the port which is not receiving the input signal (port C or D) is terminated by the impedance 16. In the middle position b of the switch 34, the first and second receivers 30 and 32 are connected to ports C and D, respectively, so that the apparatus operates as a bidirectional receiver in the same manner as the embodiment shown in FIG. 5.

Figure 7:
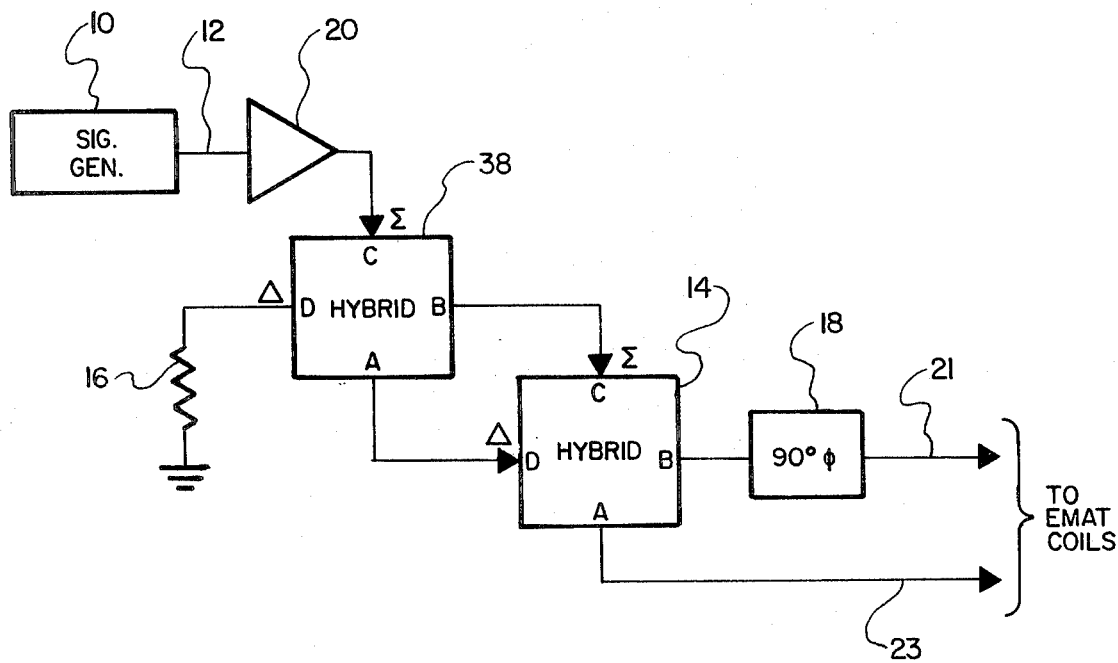
FIG. 7 is a schematic of an embodiment of the invention for generating bidirectional acoustic waves.

FIG. 7 illustrates a way in which the present invention may be utilized to provide a bidirectional generator for ultrasonic waves. In this embodiment, the hybrid 14 is connected to the EMAT coils through ports A and B and the phase delay element 18 in the same manner as described in connection with FIGS. 2-6. A second hybrid 38, however, is added, with ports A and B of the hybrid 38 being connected to the differencing port D and the summing port C of the hybrid 14, respectively. The signal generator 10 supplies a signal 12 to the transmitter 20, where the signal is amplified and thence input to the hybrid 38 through port C. Port D of the hybrid 38 is terminated through the matching impedance 16. With this arrangement, a single signal generator and transmitter produce acoustic waves travelling in two well-defined and opposite directions.

One of the best utilizations of this invention is a nondestructive testing application may be to use a unidirection transmitter which, as in the embodiment of FIG. 6, may be switched to generate ultrasonic beams in alternate directions. This transmitter would be multiplexed so that it would fire right and left alternately. The receiver would be a bidirectional receiver such as the embodiment of FIG. 5. Such a transmitter should provide a gain of 6 dB in a given direction over a conventional EMAT, while the bidirectional receiver should add an additional 3 dB of gain over the conventional arrangement, for a total gain of 9 dB.

Although some typical embodiments of the invention have been illustrated and discussed herein, numerous modifications and additional embodiments will be apparent to those skilled in the art. The advantages of the invention could also be utilized, for example, in embodiments employing different phase delays, different offsets in the coils, and with hybrids other than 180°. Furthermore, various changes may be made in the configurations, sizes, and arrangements of the components of the invention without departing from the scope of the invention. Moreover, equivalent elements may be substituted for those illustrated and described herein, parts or connections might be reversed or otherwise interchanged, and certain features of the invention might be utilized independently of the use of other features. Consequently, the examples presented herein, which are provided to teach those skilled in the art how to construct the apparatus and perform the method of this invention, should be considered as illustrative only and not inclusive, the appended claims being more indicative of the full scope of the invention.

What is claimed is:

1. An apparatus for interacting with acoustic wave energy of wavelength $\lambda$ in an electrically conductive object, comprising:
   an electromagnetic acoustic transducer, including a source of magnetic flux for producing a magnetic field extending into the object, a first periodic coil within said field, and a second periodic coil offset from said first coil within said field;
   a four port hybrid, with a first port connected to said first coil and a second port connected to said second coil; and
   a phase delay element interposed between said first port and said first coil.

2. The apparatus of claim 1, further comprising:
   a signal generator for generating an input signal at a frequency corresponding to said wavelength $\lambda$ and applying said signal to said hybrid;
   a first transmitter for receiving the portion of said signal output at said first port, amplifying said first portion, and applying said first portion to said first coil; and
   a second transmitter for receiving the portion of said signal output at said second port, amplifying said second portion, and applying said second portion to said second coil.

3. The apparatus of claim 1, further comprising:
   a signal generator for generating an input signal at a frequency corresponding to said wavelength $\lambda$; and
   a transmitter for receiving, amplifying, and applying said signal to said hybrid, such that said signal is divided by said hybrid and applied to said first and second coils.

4. The apparatus of claim 3, wherein said offset further comprises $\lambda/4$ and said phase delay element introduces a phase delay of 90°, said apparatus thereby operating to generate acoustic wave energy at said wavelength $\lambda$ in a first direction in said object when said signal is applied to a third port of said hybrid and in a direction opposite to said first direction when said signal is applied to a fourth port of said hybrid.

5. The apparatus of claim 3, wherein said hybrid comprises a first hybrid and further comprising a second four port hybrid interposed between said first hybrid and said coils such that said first coil is connected through said phase delay element to a first port of said second hybrid, said second coil is connected to a second port of said second hybrid, said first port of said first hybrid is connected to a summing third port of said second hybrid, and said second port of said first hybrid is connected to a differencing fourth port of said second hybrid.

6. The apparatus of claim 4, further comprising a switch for connecting said transmitter to said third port or said fourth port to thereby selectively generate said acoustic wave energy in alternate directions.

7. The apparatus of claim 1, further comprising a first receiver for detecting an output signal from said hybrid at a frequency corresponding to said wavelength $\lambda$.

8. The apparatus of claim 7, wherein said offset further comprises $\lambda/4$ and said phase delay element introduces a phase delay of 90°, said apparatus thereby operating to detect acoustic wave energy of said wavelength $\lambda$ propagating in a first direction in said object when said signal is detected at a third port of said hybrid and propagating in a direction opposite to said first direction when said signal is detected at a fourth port of said hybrid.

9. The apparatus of claim 8, wherein said first receiver is connected to said third port and further comprising a second receiver connected to said fourth port for detecting an output signal from said hybrid at said wavelength λ, said apparatus thereby being adapted to simultaneously detect acoustic wave energy travelling in said object in opposite directions.

10. An apparatus for generating acoustic waves of wavelength λ in an electrically conductive object, comprising:
    an electromagnetic acoustic transducer, including a source of magnetic flux for producing a magnetic field extending into the object, a first periodic coil within said field, and a second periodic coil within said field offset from said first coil by λ/4;
    a four port hybrid, with a first port connected to said first coil and a second port connected to said second coil;
    a 90° phase delay element interposed between said first port and said first coil;
    a signal generator for generating an input signal at a frequency corresponding to said wavelength λ; and
    a transmitter for receiving, amplifying, and applying said signal to said hybrid, thereby generating said waves in a first direction in said object when said signal is applied to a third port of said hybrid and in a direction opposite to said first direction when said signal is applied to a fourth port of said hybrid.

11. An apparatus for detecting acoustic waves of wavelength λ in an electrically conductive object, comprising:
    an electromagnetic acoustic transducer, including a source of magnetic flux for producing a magnetic field extending into the object, a first periodic coil within said field, and a second periodic coil within said field offset from said first coil by λ/4;
    a four port hybrid, with a first port connected to said first coil and a second port connected to said second coil;
    a 90° phase delay element interposed between said first port and said first coil;
    a first receiver connected to a third port of said hybrid to detect acoustic wave energy at a frequency corresponding to said wavelength λ propagating in a first direction in said object; and
    a second receiver connected to a fourth port of said hybrid to detect acoustic wave energy at a frequency corresponding to said wavelength λ propagating in a direction opposite to said first direction in said object.

12. A method of generating acoustic energy of wavelength λ in an electrically conductive object, comprising the steps of:
    establishing a magnetic field extending into the object;
    positioning a first periodic coil within the field;
    positioning a second periodic coil within the field and offset from the first coil;
    connecting first and second ports of a four port hybrid to the first and second coils, respectively;
    introducing a phase delay between the hybrid and the first coil;
    generating an input signal at a frequency corresponding to the wavelength λ; and
    transmitting the input signal to a third port of the hybrid.

13. The method of claim 12, wherein the step of positioning the second coil further comprises positioning the second coil offset from the first coil by λ/4; and
    the step of introducing a phase delay further comprises introducing a phase delay of 90° between the hybrid and the first coil.

14. A method of detecting acoustic energy of wavelength λ in an electrically conductive object, comprising the steps of:
    establishing a magnetic field extending into the object;
    positioning a first periodic coil within the field;
    positioning a second periodic coil within the field and offset from the first coil;
    connecting first and second ports of a four port hybrid to the first and second coils, respectively;
    introducing a phase delay between the hybrid and the first coil; and
    connecting a first receiver to a third port of the hybrid.

15. The method of claim 14, wherein:
    the step of positioning the second coil further comprises positioning the second coil offset from the first coil by λ/4; and
    the step of introducing a phase delay further comprises introducing a phase delay of 90° between the hybrid and the first coil.

16. The method of claim 15, further comprising the step of connecting a second receiver to a fourth port of the hybrid.

* * * * *